US006582688B1

(12) United States Patent
Broutin et al.

(10) Patent No.: US 6,582,688 B1
(45) Date of Patent: Jun. 24, 2003

(54) METHOD FOR EXTRACTING COMPOUNDS OF FURAN LIPIDS AND POLYHYDROXYLATED FATTY ALCOHOLS OF AVOCADO, COMPOSITION BASED ON SAID COMPOUNDS, AND THERAPEUTIC, COSMETICAL OR FOOD USE OF SAID COMPOUNDS

(75) Inventors: Nicole Broutin, Alluyes (FR); Jacques Legrand, Neuilly sur Eure (FR); Antoine Piccirilli, Versailles (FR)

(73) Assignee: Pharmascience, Courbevoie (FR)

( * ) Notice: Subject to any disclaimer, the term of this patent is extended or adjusted under 35 U.S.C. 154(b) by 0 days.

(21) Appl. No.: 10/088,077

(22) PCT Filed: Sep. 20, 2000

(86) PCT No.: PCT/FR00/02601

§ 371 (c)(1),
(2), (4) Date: Mar. 20, 2002

(87) PCT Pub. No.: WO01/21605

PCT Pub. Date: Mar. 29, 2001

(30) Foreign Application Priority Data

Sep. 22, 1999 (FR) .............................. 99 11846

(51) Int. Cl.⁷ ........................ A01N 65/00; A61K 35/78; A61K 31/74; A23L 2/02
(52) U.S. Cl. .................... 424/78.03; 424/725; 424/757; 424/769; 426/51
(58) Field of Search ............... 424/78.03, 725, 424/757, 769; 426/51

(56) References Cited

U.S. PATENT DOCUMENTS 5,468,490 A * 11/1995 Huber et al. ............. 424/78.03
6,086,903 A * 7/2000 Trinh et al. .............. 424/78.03
6,133,313 A * 10/2000 Thomson et al. ........... 514/461
6,355,280 B1 * 3/2002 Segal et al. ................ 424/757

FOREIGN PATENT DOCUMENTS

| CA | 2213112 A1 | 2/1999 |
| EP | 0 493 144 A1 | 7/1992 |
| EP | 0 775 480 A1 | 5/1997 |
| FR | 2 678 614 A1 | 1/1993 |
| FR | 2 678 632 A1 | 1/1993 |

OTHER PUBLICATIONS

Rancurel, A.; "L'avocat: son huile et son insaponifiable. Utilisation cosmeteque"; *Perfums, Cosmetiques, Aromes;* No. 61, Feb.–Mar. 1985; Societe D'Expansion Technique et Economique S.A.; Paris, France; pp 91–95.

Farines, M., et al.; "Influence of Avocado Oil Processing on the Nature of Some Unsaponifiable Constituents"; *Journal of the American Oil Chemists' Society,* vol. 72, No. 4, 1995; American Oil Chemists' Society; Champaign; U.S.; pp 473–476.

* cited by examiner

*Primary Examiner*—Herbert J. Lilling
(74) *Attorney, Agent, or Firm*—Foley & Lardner

(57) ABSTRACT

The invention concerns a method for selectively extracting furan lipids and polyhydroxylated fatty alcohols of avocado, characterised in that it comprises steps which consist in: preparing an unsaponifiable matter of avocado; then in subjecting the unsaponifiable matter of avocado to a step of molecular distillation using adjusted temperature and pressure means to obtain either a distillate comprising mainly furan lipids and polyhydroxylated fatty alcohols of avocado. Said method enables in particular to extract selectively furan lipids of avocado having a furan lipid content of more than 80 wt. %, even close to 98%.

29 Claims, No Drawings

METHOD FOR EXTRACTING COMPOUNDS OF FURAN LIPIDS AND POLYHYDROXYLATED FATTY ALCOHOLS OF AVOCADO, COMPOSITION BASED ON SAID COMPOUNDS, AND THERAPEUTIC, COSMETICAL OR FOOD USE OF SAID COMPOUNDS

The present invention relates to a novel process for extracting furan lipid compounds and polyhydroxylated fatty alcohols from avocado, and also to a pharmaceutical or cosmetic composition based on these compounds and to the use of these compounds for manufacturing a medicinal product, in a cosmetic treatment method and as a food additive.

Avocado comprises, as is known, particular lipids of furan type, the main component of which is a linoleic furan:

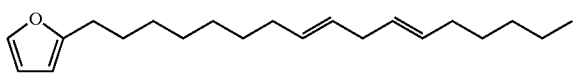

Furan compound H7

The furan derivatives of avocado oil have been described in particular in Farines, M. et al., 1995, J. of Am. Oil Chem. Soc. 72, 473.

It is currently well established that the presence of these furan compounds in the leaves or the fruit depends not only on the variety (the varieties Hass and Fuerte being the richest in furan compounds), but also on the method for obtaining the oil or another plant extract of avocado (ethanolic or hexane extract of avocado leaves).

Specifically, it is known that these furan lipids are metabolites of compounds that are initially present in the fruit and the leaves, which, due to the effect of heat, become dehydrated and cyclize into furan derivatives.

For example, linoleic furan is derived from the thermal transformation of the following precursor:

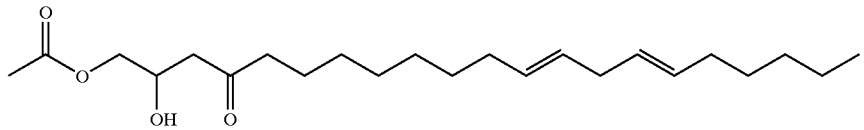

Precursor P1H7

Moreover, certain compounds initially present in avocado fruit and leaves may be in the form of nonacetylated polyhydroxylated fatty alcohols, such as the following compound:

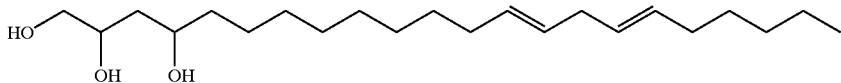

The polyhydroxylated fatty alcohol content in the fruit depends mainly on the climatic conditions, the quality of the soil, the season and the maturity of the fruit on harvesting.

In general, the furan lipids of avocado are compounds that are unique in the plant kingdom and are desired above all for their pharmacological, cosmetic or even nutritional properties.

However, the known techniques for obtaining these specific compounds from avocado fruit or from the oil of avocado fruit amount either to preparative chromatography or to industrial processes that allow these furan lipids to be obtained only as a mixture with the other unsaponifiable compounds of avocado, in a maximum content of furan lipids that is at best between 50% and about 65% by weight only.

In addition, the known industrial processes require a preliminary step of molecular distillation of the oil of the fruit to obtain the furan lipids in contents that are nevertheless still unsatisfactory. This preliminary step requires the use of high temperatures, such as temperatures above 180° C. for pressures of the order of $10^{-3}$ mmHg, which, in industrial terms, involves a large consumption of energy.

More particularly, the production of furan lipids of higher purity by molecular distillation of the oil of the fruit ("crude pressed oil") is industrially difficult given the very acidic nature of the oil (acid number of about 6 to 10 mg KOH/g), necessitating a preliminary neutralization by at least partially refining the oil. Furthermore, such a refining operation, even partial, entails a consequent loss of furan lipids and thus a reduction in the final yield of these desired compounds.

It has now been found, entirely surprisingly and unexpectedly, that the drawbacks of the prior art described above can be overcome by carrying out a specific process for obtaining a selective extraction of the furan lipids of avocado with a content of more than 80% by weight of furan lipids, or even close to 98%.

Moreover, according to one particular embodiment of the process according to the invention, a selective extraction is advantageously obtained not only of the furan lipids, but also of the polyhydroxylated fatty alcohols of avocado.

What is more, the process according to the invention comprises a step of molecular distillation in which the temperature and pressure settings may be markedly lower than those of the abovementioned prior art.

One subject of the present invention is thus a process for selectively extracting the furan lipids and polyhydroxylated fatty alcohols of avocado, characterized in that it comprises the steps consisting in preparing an unsaponifiable material from avocado, and then in subjecting the unsaponifiable material from avocado to a step of molecular distillation using temperature and pressure means that are adjusted so as to obtain either a distillate mainly comprising furan lipids of avocado, or a distillate mainly comprising furan lipids and polyhydroxylated fatty alcohols of avocado.

According to the invention, the expression "furan lipids of avocado" means the compounds corresponding to the formula:

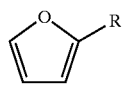

in which R is a saturated $C_{11}$–$C_{19}$ and preferably $C_{13}$–$C_{17}$ linear hydrocarbon-based chain or a chain comprising one or more ethylenic or acetylenic unsaturations.

According to the invention, the expression "polyhydroxylated fatty alcohol of avocado" means a polyol in the form of a saturated $C_{17}$–$C_{21}$ linear hydrocarbon-based main chain or a chain comprising one or more ethylenic or acetylenic unsaturations, and comprising at least two hydroxyl groups, the hydroxyl groups being mainly located on one portion of the main chain, preferably toward one of the two ends of the main chain, the other portion of this main chain thus constituting the "fatty" chain (hydrophobic portion) of the polyol.

The unsaponifiable material is the fraction of a fatty substance which, after the prolonged action of an alkaline base, remains insoluble in water and may be extracted with an organic solvent. Five major groups of substances are present in the majority of the unsaponifiable materials from plant oils: saturated or unsaturated hydrocarbons, aliphatic or terpenic alcohols, sterols, tocopherols, carotenoid and xanthophilic pigments.

A comparison of the contents of unsaponifiable materials from various plant oils: soybean, cotton, coconut, olive and avocado, shows a very large content of unsaponifiable material from avocado oil obtained by extraction according to various known processes. Typically, the contents obtained range from 2 to 7% of unsaponifiable material in avocado oil, compared with 0.5% in coconut oil, 1% in soybean oil and 1% in olive oil. The unsaponifiable material from avocado may be prepared by extraction starting with avocado oil.

The known processes for obtaining avocado oil are mainly the following:
- either the fresh pulp is pressed in the presence of a water-absorbing intermediary fibrous substance such as coffee husk in a cage press, and the emulsion of oil and water obtained is then separated out by settling and/or centrifugation;
- or the fresh pulp is ground and is placed in contact with a suitable organic solvent (for example a methanol/chloroform mixture) and the oil is then recovered by evaporating off the solvent.

The avocado oil thus obtained is then subjected to an extraction of the unsaponifiable material, in a known manner.

Several processes have been described for extracting the unsaponifiable material from a plant oil. All preferably adopt saponification with potassium hydroxide or sodium hydroxide in alcoholic medium, preferably ethanolic medium, followed by one or more extractions with a suitable organic solvent, for example petroleum ether, ethyl ether or any other suitable solvent that is immiscible with the aqueous-alcoholic solution.

The extraction solution obtained is then preferably centrifuged, filtered and then washed with water to remove the residual traces of alkalinity. Next, the extraction solvent is carefully evaporated off to recover the unsaponifiable material. Needless to say, additional operations known to those skilled in the art, such as a deodorization step, may also be included.

Preferably, the unsaponifiable material from avocado is prepared from the fruit that has been heat-treated beforehand, before extraction of the oil and saponification, as described in particular in patent application FR-91/08301.

This heat treatment consists of a controlled drying of the fruit, which is preferably fresh, for at least four hours, advantageously at least 10 hours and preferably between about 24 and about 48 hours, at a temperature preferably of at least about 80° C. and preferably between about 80 and about 120° C.

It is clearly understood that the drying time and temperature are two mutually linked parameters as regards the expected result of the heat treatment, which is to promote the cyclization of the furan lipid precursors.

Finally, before its saponification, the oil may be pre-enriched in unsaponifiable material by separating out a majority of the constituents of the unsaponifiable material that are recovered in a concentrate. Various methods may be used: cold crystallization, liquid-liquid extraction, molecular distillation. Preliminary concentration of the unsaponifiable material of the oil makes it possible to reduce the consumption of oil during the saponification. Molecular distillation is particularly preferred, and is preferably performed at a temperature of between about 180 and about 230° C. while maintaining a pressure of between $10^{-3}$ and $10^{-2}$ mmHg and preferably of the order of $10^{-3}$ mmHg. The concentration of unsaponifiable material in the distillate may be up to 60%.

In general, the average composition of an unsaponifiable material from avocado obtained mainly by controlled drying of the fruit, extraction of the oil by cold pressing, preliminary molecular distillation of the oil before saponification with ethanolic potassium hydroxide, extraction of the unsaponifiable material in a countercurrent column with an organic solvent, filtration, washing, desolvation and deodorization, is as follows (in percentages by weight relative to the total weight of the unsaponifiable material):

| | |
|---|---|
| polyhydroxylated fatty alcohols | 5–25% |
| furan lipids | 50–70% |
| sterols | 2–4% |
| squalene | 0.5–5% |
| others | 5–20% (1) |

(1) free fatty acids, hydrocarbons, tocopherols, fatty ketones and heavy pigments.

According to the invention, the unsaponifiable material from avocado obtained as described above is then subjected to a step of molecular distillation.

According to one particularly preferred embodiment of the present invention, this step of molecular distillation, combination of which with the preliminary step of preparing the unsaponifiable material constitutes an essential characteristic of the present process, is performed with temperature means adjusted for a temperature of between 100 and 160° C. and pressure means adjusted for a pressure of between $10^{-3}$ and $5 \times 10^{-2}$ mmHg.

In particular, the temperature means are adjusted for a temperature of between 100 and 140° C. and the pressure means are adjusted for a pressure of between $10^{-3}$ and $5 \times 10^{-2}$ mmHg, so as to obtain a distillate mainly comprising furan lipids of avocado.

Moreover, according to one advantageous variant of the present process, the temperature means are adjusted for a temperature of between 130 and 160° C. and the pressure means are adjusted for a pressure of between $10^{-3}$ and $5 \times 10^{-2}$ mmHg, so as to obtain a distillate mainly comprising furan lipids of avocado and polyhydroxylated fatty alcohols of avocado.

This step of molecular distillation of the unsaponifiable material, and also any other molecular distillations that may be carried out in the process of the invention, as described above, are preferably performed using a device chosen from molecular distillation devices of centrifugal type and molecular devices of scraped film type.

Molecular distillation devices of centrifugal type are known to those skilled in the art. For example, patent application EP-0 493 144 describes a molecular distillation device of this type. In general, the product to be distilled is spread in a thin layer onto the heated surface (hot surface) of a conical rotor rotating at high speed. The distillation chamber is placed under vacuum. Under these conditions, there is evaporation rather than boiling, from the hot surface, of the constituents of the unsaponifiable material, the advantage being that the oil and the unsaponifiable material (these products being notoriously fragile) are not degraded during the evaporation.

Molecular distillation devices of scraped film type, which are also known to those skilled in the art, comprise a distillation chamber containing a rotating doctor blade, allowing the product to be distilled to be spread continuously over the evaporation surface (hot surface). The product vapors are condensed by means of a cold finger, placed in the center of the distillation chamber. The peripheral feed and vacuum systems are very similar to those of a centrifugal distillation device (feed pumps, vane vacuum pumps, oil diffusion pumps, etc.). The recovery of the residues and the distillates in glass flasks takes place by gravitational flow.

A subject of the present invention is also a pharmaceutical composition, characterized in that it comprises at least one active principle chosen from the group consisting of distillates mainly comprising furan lipids of avocado and distillates mainly comprising furan lipids and polyhydroxylated fatty alcohols of avocado, as obtained by the process described above, and at least one pharmaceutically acceptable excipient.

More particularly, a subject of the present invention is the use of at least one compound chosen from the group consisting of distillates mainly comprising furan lipids of avocado and distillates mainly comprising furan lipids and polyhydroxylated fatty alcohols of avocado, as obtained by the process described above, for the manufacture of a medicinal product intended for treating articular complaints, more particularly for treating arthrosis and for treating arthritis (that is to say rheumatoid arthritis, psoriatic arthritis, Lyme's arthritis and/or any other type of arthritis).

The medicinal product thus prepared may be intended for treating periodontal complaints, and in particular for treating periodontitis.

This medicinal product may moreover be intended for treating osteoporosis.

In addition, this medicinal product may be intended for modifying the differentiation of nerve cells that is induced with NGF. According to the invention, the term "modifying" means the action of increasing or reducing the differentiation of nerve cells that is induced with NGF.

Finally, this medicinal product may be intended for tissue repair, and in particular for repairing skin tissue, especially in the context of a dermatological use.

Another subject of the present invention is a cosmetic composition, especially a dermocosmetic composition, characterized in that it comprises at least one cosmetically active principle chosen from the group consisting of distillates mainly comprising furan lipids of avocado and distillates mainly comprising furan lipids and polyhydroxylated fatty alcohols of avocado, as obtained by the process described above, and at least one cosmetically acceptable excipient.

Finally, the present invention also relates to a cosmetic method for treating the skin, neighboring mucous membranes and/or integuments, characterized in that a cosmetic composition comprising at least one compound chosen from the group consisting of distillates mainly comprising furan lipids of avocado and distillates mainly comprising furan lipids and polyhydroxylated fatty alcohols of avocado, as obtained by the process described above, and at least one cosmetically acceptable vehicle such as the vehicles generally used in the field of cosmetic products, is applied to the skin, neighboring mucous membranes and/or integuments.

Preferably, it is a cosmetic method for treating scars on the skin, the intrinsic ageing of the skin (that is to say ageing of the skin not resulting predominantly from an action external to the skin) and a cosmetic method for treating skin that has been subjected to actinic radiation, especially ultraviolet radiation.

Preferably, the unsaponifiable material from plant oil is present in the cosmetic composition in a proportion of between about 0.1 and about 10% by weight relative to the total weight of the cosmetic composition.

Finally, a subject of the present invention is a food additive, characterized in that it comprises at least one compound chosen from the group consisting of distillates mainly comprising furan lipids of avocado and distillates mainly comprising furan lipids and polyhydroxylated fatty alcohols of avocado, as obtained by the process described above.

Finally, the present invention relates to the use of at least one compound chosen from the group consisting of distillates mainly comprising furan lipids of avocado and distillates mainly comprising furan lipids and polyhydroxylated fatty alcohols of avocado, as obtained by the selective extraction process described above, as an additive in a food for humans and/or animals, in a proportion of said compound of between about 0.1 and about 20% by weight relative to the total weight of the food.

The following examples are intended to illustrate the present invention and should not in any way be interpreted as possibly limiting its scope.

Unless otherwise specified, the percentages indicated in the following examples are percentages by weight.

Example 1: Preparation of an Unsaponifiable Material from Avocado 100 g of avocado cut into slices about 5 mm thick are subjected to the following operations:

1.1) Heat Treatment of the Fruit

The sliced fruit is placed in an oven set at 80° C. for 24 hours, and is then ground.

1.2) Production of the Oil

The powder obtained in the preceding step is extracted with hexane by cold-pressing in a "KOMET" screw press. The cake is removed and the hexanic solution is evaporated off under reduced pressure. The oil recovered is filtered through a Büchner funnel and then stored under nitrogen. 20 g of avocado oil are thus obtained.

1.3) Concentration

A scraped-film distillation device as described above, sold by the company Leybold under the name "KDL 4", is used. It is a glass device, equipped with a distillation chamber comprising a rotating doctor blade, allowing the product to be treated to be spread continuously over the evaporation surface (hot surface). The product vapors are condensed by means of a cold finger, placed in the center of the distillation chamber. The peripheral feed and vacuum systems are very similar to those of a centrifugal distillation device (feed pumps, vane vacuum pumps, oil diffusion pumps, etc.). The recovery of the residues and the distillates in glass flasks takes place by gravitational flow.

The distillation temperature is about 230° C. with a pressure of the order of $10^{-3}$ mmHg. The rotation speed of the shaft is 200 rpm and the feed rate is 7 ml/min.

1.4) Saponification 50 g of oil concentrate obtained as in the preceding step are mixed with 25 ml of 12N potassium hydroxide and 100 ml of ethanol and refluxed for 4 hours. 175 ml of water are added to the aqueous-alcoholic phase, followed by addition of 175 ml of dichloroethane, and the mixture is stirred and the phases are then allowed to separate by settling. The organic phase is then recovered. This operation is repeated 5 to 6 times. The organic phases are combined and washed with water, and the solvent is evaporated off. 20 g of unsaponifiable material are thus obtained. Needless to say, for an industrial-scale preparation, the steps of extraction in a separating funnel can be replaced with a continuous extraction in a continuous liquid-liquid extraction machine such as a pulsed column, a decanting mixer or equivalents.

Example 2: Molecular Distillation of an Unsaponifiable Material Rich in Polyhydroxylated Fatty Alcohols An unsaponifiable material is prepared as described above. The analysis of this unsaponifiable material shows that it is rich in polyhydroxylated fatty alcohols (about 25%). Its composition is as follows:

| | |
|---|---|
| polyhydroxylated fatty alcohols | 24.3% |
| furan lipids | 55.5% |
| sterols | 3.1% |
| squalene | 1.4% |
| others | 15.7%(1) |

(1) free fatty acids, hydrocarbons, tocopherols, fatty ketones and heavy pigments.

2.1) Laboratory Distillation

This unsaponifiable material is subjected to a molecular distillation using the same "KDL4" scraped-film device from the company Leybold described above.

However, the distillation conditions are as follows:

| | |
|---|---|
| hot-surface temperature: 108° C. | |
| pressure: $10^{-3}$ mmHg | |
| rotation speed of the shaft: 240 rpm | |
| feed rate of unsaponifiable material from avocado: 400 ml/h | |

Distillation Yield: 48.6%.

Composition of the distillate:

| | |
|---|---|
| polyhydroxylated fatty alcohols: n.m. | |
| furan lipids | 99.1% |
| sterols | n.m. |
| squalene | n.m. |
| others | 0.9%(1) |

(1) free fatty acids, hydrocarbons and fatty ketones ("n.m.": not measurable, that is to say a content of less than 0.05%).

This is thus a distillate that is very rich in furan lipids since the content of these lipids exceeds 99%.

2.2) Pilot-scale Molecular Distillation

The same unsaponifiable material from avocado is distilled in a pilot molecular distillation device (15–25 kg/h) of centrifugal type, operating continuously, under a vacuum of between 0.01 and 0.05 mm of mercury, and at a temperature in the range from 100 to 150° C.

The results obtained at various temperatures and pressures are collated in tables 1 and 2 below.

TABLE 1

Extraction of the furan lipids by molecular distillation of an unsaponifiable material from avocado that is rich in polyhydroxylated fatty alcohols

| Sample | Temperature (T° C.) | Pressure (mmHg) | Feed rate (kg/h) | Degree of distillation (%) | Content of furan lipids in the distillate (%) |
|---|---|---|---|---|---|
| 1 | 129 | 0.020 | 13.3 | 60.0 | 93.2 |
| 2 | 123 | 0.025 | 13.5 | 53.6 | 96.2 |
| 3 | 112 | 0.050 | 12.9 | 47.0 | 97.7 |

The degree of distillation is defined as follows: it is the mass ratio, relative to 100%, of the mass of the distillate to the sum (mass of the distillate+mass of the residue).

The results collated in table 1 show that the molecular distillation of an unsaponifiable material from avocado makes it possible, simply and in a substantial yield, to prepare a fraction that is very rich in furan lipids of avocado (content of greater than 97%).

In an identical manner, the results of the tests collated in table 2 show that it is also possible to obtain fractions that are selectively enriched in avocado furans and polyhydroxylated fatty alcohols.

TABLE 2

Extraction of the furan lipids and polyhydroxylated fatty alcohols by molecular distillation of an unsaponifiable material from avocado that is rich in polyhydroxylated fatty alcohols

| Sample | T (° C.) | Pressure (mmHg) | Feed rate (kg/h) | Degree of distillation (%) | Content of furan lipids in the distillate (%) | Content of polyhydroxylated fatty alcohols in the distillate (%) |
|---|---|---|---|---|---|---|
| 4 | 150 | 0.015 | 12.8 | 79.8 | 73.5 | 22.0 |
| 5 | 137 | 0.025 | 12.6 | 85.5 | 66.9 | 25.5 |

In conclusion, this set of tests shows that it is possible, by molecular distillation of an unsaponifiable material from avocado, that is rich in polyhydroxylated fatty alcohols, to prepare distillates of very high purity, selectively comprising a high content of furan lipids (purity greater than 97%) or a high content of furan lipids with polyhydroxylated fatty alcohols (sum of the contents of furan lipids and of polyhydroxylated fatty alcohols greater than 95%).

Example 3: Molecular Distillation of an Unsaponifiable Material that is Low in Polyhydroxylated Fatty Alcohols An unsaponifiable material is prepared as described above. The analysis of this unsaponifiable material shows that it is low in polyhydroxylated fatty alcohols (about 4%). Its composition is as follows:

| | |
|---|---|
| polyhydroxylated fatty alcohols | 3.7% |
| furan lipids | 68.7% |
| sterols | 6.6% |
| squalene | 1.4% |
| others | 19.6%(1) |

(1) free fatty acids, hydrocarbons, tocopherols, fatty ketones and heavy pigments.

3.1) Laboratory Distillation

This unsaponifiable material is subjected to a molecular distillation using the same "KDL4" scraped-film device from the company Leybold as that already described above.

The distillation conditions are as follows:

hot-surface temperature: 108° C.

pressure: $10^{-3}$ mmHg rotation speed of the shaft: 240 rpm feed rate of unsaponifiable material from avocado: 400 ml/h.

Yield of distillate: 50.8%.

Composition of the distillate:

| | |
|---|---|
| polyhydroxylated fatty alcohols: | 0.2% |
| furan lipids | 94.8% |
| sterols | 0.1% |
| squalene | 0.2% |
| others | 4.7%. |

This is thus a distillate that is very rich in furan lipids since its content of these lipids exceeds 94%.

3.2) Pilot-scale Molecular Distillation

The same unsaponifiable material from avocado is distilled in a pilot molecular distillation device (15–25 kg/h) of centrifugal type, operating continuously, under a vacuum of between 0.01 and 0.05 mm of mercury, and at a temperature in the range between 100 and 140° C. The results obtained at various temperatures and pressures are collated in table 3 below.

TABLE 3

Extraction of the furan lipids by molecular distillation of an unsaponifiable material from avocado that is low in polyhydroxylated fatty alcohols

| Sample | T (° C.) | Pressure (mmHg) | Feed rate (kg/h) | Degree of distillation (%) | Content of furan compounds in the distillate (%) |
|---|---|---|---|---|---|
| 1 | 115 | 0.015 | 20.4 | 47.8 | 94.3 |
| 2 | 126 | 0.015 | 18.6 | 65.8 | 94.2 |
| 3 | 137 | 0.015 | 18.5 | 71.3 | 93.8 |

The results collated in table 3 show that the molecular distillation of an unsaponifiable material from avocado makes it possible, simply and in a substantial yield, to prepare a distillate that is very rich in furan lipids of avocado (content of greater than 94%).

What is claimed is:

1. A process for selectively extracting the furan lipids and polyhydroxylated fatty alcohols of avocado, characterized in that it comprises the steps consisting in preparing an unsaponifiable material from avocado, and then in subjecting the unsaponifiable material from avocado to a step of molecular distillation using temperature and pressure means that are adjusted so as to obtain either a distillate mainly comprising furan lipids of avocado, or a distillate mainly comprising furan lipids and polyhydroxylated fatty alcohols of avocado.

2. The process as claimed in claim 1, characterized in that, for the molecular distillation step following that of preparation of the unsaponifiable material, the temperature means are adjusted for a temperature of between 100 and 160° C. and the pressure means are adjusted for a pressure of between $10^{-3}$ and $5 \times 10^{-2}$ mmHg.

3. The process as claimed in claim 1, characterized in that, for the molecular distillation step following that of preparation of the unsaponifiable material, the temperature means are adjusted for a temperature of between 100 and 140° C. and the pressure means are adjusted for a pressure of between $10^{-3}$ and $5 \times 10^{-2}$ mmHg, so as to obtain a distillate mainly comprising furan lipids of avocado.

4. The process as claimed in claim 1, characterized in that, for the molecular distillation step following that of preparation of the unsaponifiable material, the temperature means are adjusted for a temperature of between 130 and 160° C. and the pressure means are adjusted for a pressure of between $10^{-3}$ and $5 \times 10^{-2}$ mmHg, so as to obtain a distillate mainly comprising furan lipids of avocado and polyhydroxylated fatty alcohols of avocado.

5. The process as claimed in claim 1, characterized in that the unsaponifiable material from avocado is prepared from the fruit that has been heat-treated beforehand.

6. The process as claimed in claim 5, characterized in that the fruit is heat-treated beforehand by controlled drying at a temperature of at least about 80° C. for a period of at least about four hours.

7. The process as claimed in claim 1, characterized in that the unsaponifiable material from avocado is prepared from the oil of the fruit that is enriched beforehand in unsaponifiable material by molecular distillation.

8. The process as claimed in claim 7, characterized in that the molecular distillation of the oil of the fruit is performed at a temperature of between about 180 and about 230° C. and at a pressure of between about $10^{-3}$ and about $10^{-2}$ mmHg.

9. The process as claimed in claim 1, characterized in that the molecular distillation is performed using a device chosen from molecular distillation devices of centrifugal type and molecular devices of scraped-film type.

10. A pharmaceutical composition, characterized in that it comprises at least one active principle chosen from the group consisting of distillates mainly comprising furan lipids of avocado and distillates mainly comprising furan lipids and polyhydroxylated fatty alcohols of avocado, as obtained by the process as claimed in claim 1, and at least one pharmaceutically acceptable excipient.

11. A cosmetic composition comprising at least one cosmetically active principle chosen from the group consisting of distillates mainly comprising furan lipids of avocado and distillates mainly comprising furan lipids and polyhydroxylated fatty alcohols of avocado, as obtained by the process as claimed in claim 1, and at least one cosmetically acceptable excipient.

12. A cosmetic method for treating the skin, neighboring mucous membranes and/or integuments, characterized in that a cosmetic composition comprising at least one cosmetically active compound chosen from the group consisting of distillates mainly comprising furan lipids of avocado and distillates mainly comprising furan lipids and polyhydroxylated fatty alcohols of avocado, as obtained by the process as claimed in claim 1, and at least one cosmetically acceptable vehicle, is applied to the skin, neighboring mucous membranes and/or integuments.

13. The method as claimed in claim 12, for the cosmetic treatment of scars on the skin.

14. The method as claimed in claim 12, for the cosmetic treatment of intrinsic aging of the skin.

15. The method as claimed in claim 12, for the cosmetic treatment of skin that has been subjected to actinic radiation.

16. The method as claimed in claim 12, wherein the cosmetically active compound is present in the cosmetic composition in a proportion of between about 0.1 and about 10% by weight relative to the total weight of the cosmetic composition.

17. A food additive, comprising at least one composition chosen from the group consisting of distillates mainly comprising furan lipids of avocado and distillates mainly comprising furan lipids and polyhydroxylated fatty alcohols of avocado, as obtained By the process as claimed in claim 1.

18. A method of treating articular complaints in a patient comprising administering to the patient compounds extracted using the method of claim 1, said compounds chosen from the group consisting of distillates mainly comprising furan lipids of avocado and distillates mainly comprising furan lipids and polyhydroxylated fatty alcohols of avocado.

19. A method according to claim 18, wherein the articular complaint is arthrosis.

20. A method according to claim 18, wherein the articular complaint is arthritis.

21. A method of treating periodontal conditions comprising administering to a patient compounds extracted using the method of claim 1, said compounds chosen from the group consisting of distillates mainly comprising furan lipids of avocado and distillates mainly comprising furan lipids and polyhydroxylated fatty alcohols of avocado.

22. A method according to claim 21, wherein the periodontal conditions is periodontitis.

23. A method of treating osteoporosis comprising administering to a patient compounds extracted using the method of claim 1, said compounds chosen from the group consisting of distillates mainly comprising furan lipids of avocado and distillates mainly comprising furan lipids and polyhydroxylated fatty alcohols of avocado.

24. A method modifying the differentiation of nerve cells induced with NGF comprising administering to a patient compounds extracted using the method of claim 1, said compounds chosen from the group consisting of distillates mainly comprising furan lipids of avocado and distillates mainly comprising furan lipids and polyhydroxylated fatty alcohols of avocado.

25. A method of repairing tissue conditions comprising administering to a patient compounds extracted using the method of claim 1, said compounds chosen from the group consisting of distillates mainly comprising furan lipids of avocado and distillates mainly comprising furan lipids and polyhydroxylated fatty alcohols of avocado.

26. A method according to claim 25, wherein the tissue is skin tissue.

27. A method of modifying food with a food additive comprising:

extracting compounds using the method of claim 1, said compounds chosen from the group consisting of distillates mainly comprising furan lipids of avocado and distillates mainly comprising furan lipids and polyhydroxylated fatty alcohols of avocado;

adding said compounds to food in proportion of about 0.1 to about 20% by weight relative to the total weight of food.

28. A cosmetic composition according to claim 11, wherein the cosmetic composition is a dermocosmetic composition.

29. The method of claim 15, wherein the actinic radiation is UV radiation.

* * * * *

UNITED STATES PATENT AND TRADEMARK OFFICE
CERTIFICATE OF CORRECTION

PATENT NO. : 6,582,688 B1  
DATED : June 24, 2003  
INVENTOR(S) : Nicole Broutin, Jacques Legrand and Antoine Piccirilli It is certified that error appears in the above-identified patent and that said Letters Patent is hereby corrected as shown below:

<u>Title page,</u>  
Item [73], Assignee, please delete and insert as follows:  
-- [73] Assignee: Laboratoires Expanscience, Courbevoie Cedex (FR) --

<u>Column 9,</u>  
Line 64, delete "characterized in that it comprises" and insert -- comprising --;  
Line 65, delete "consisting in", insert -- of --; and delete "in"

<u>Column 10,</u>  
Lines 5, 10 and 17, delete "characterized in that," and insert -- wherein --  
Lines 25, 28, 33, 36, 40, 44 and 59, delete "characterized in that" and insert -- wherein --  
Line 61, delete "compound", and insert -- composition --

<u>Column 11,</u>  
Line 8, delete "compound", and insert -- composition --  
Lines 18 & 19 , 28 & 30 and 37 & 38, delete "compounds", and insert  
-- compositions --.

<u>Column 12,</u>  
Lines 7 & 8, 13 & 14 and 23 & 28, delete "compounds", and insert -- compositions --.

Signed and Sealed this

Eleventh Day of May, 2004

JON W. DUDAS  
*Acting Director of the United States Patent and Trademark Office*